(12) United States Patent
Popoola et al.

(10) Patent No.: US 7,790,216 B2
(45) Date of Patent: Sep. 7, 2010

(54) METHOD FOR PRODUCING A ZIRCONIA-LAYERED ORTHOPEDIC IMPLANT COMPONENT

(75) Inventors: Oludele Popoola, Granger, IN (US); Jeffrey P. Anderson, Warsaw, IN (US); Michael E. Hawkins, Columbia City, IN (US); Todd S. Johnson, Fort Wayne, IN (US); H. Ravindranath Shetty, Warsaw, IN (US)

(73) Assignee: Zimmer Technology, Inc., Warsaw, IN (US)

( * ) Notice: Subject to any disclaimer, the term of this patent is extended or adjusted under 35 U.S.C. 154(b) by 1394 days.

(21) Appl. No.: 11/109,426

(22) Filed: Apr. 19, 2005

(65) Prior Publication Data

US 2006/0233944 A1 Oct. 19, 2006

(51) Int. Cl.
- *A61L 27/04* (2006.01)
- *B05D 3/02* (2006.01)
- *C23C 14/14* (2006.01)
- *A61F 2/28* (2006.01)

(52) U.S. Cl. .................. 427/2.27; 427/2.1; 427/2.24; 427/523; 427/526; 427/528; 623/11.11; 623/23.56

(58) Field of Classification Search ... 623/11.11–23.63; 427/331, 372.2, 2.24
See application file for complete search history.

(56) References Cited

U.S. PATENT DOCUMENTS

| | | | |
|---|---|---|---|
| 2,987,352 A | 6/1961 | Watson | |
| 3,677,795 A | 7/1972 | Bokros et al. | |
| 4,145,764 A | 3/1979 | Suzuki et al. | |
| 4,487,808 A | 12/1984 | Lambert | |
| 4,671,824 A | 6/1987 | Haygarth | |
| 5,037,438 A * | 8/1991 | Davidson | 623/22.15 |
| 5,258,022 A * | 11/1993 | Davidson | 623/2.42 |
| 5,316,594 A | 5/1994 | Kemp | |
| 5,324,009 A | 6/1994 | Kemp | |
| 5,383,934 A * | 1/1995 | Armini et al. | 427/529 |
| 5,399,207 A | 3/1995 | Kemp | |
| 5,409,703 A | 4/1995 | McAnalley et al. | |
| 5,464,440 A | 11/1995 | Johansson | |
| 5,509,899 A | 4/1996 | Fan et al. | |
| 5,612,052 A | 3/1997 | Shalaby | |
| 5,714,159 A | 2/1998 | Shalaby | |
| 5,980,974 A * | 11/1999 | Armini et al. | 427/2.27 |
| 6,080,488 A | 6/2000 | Hostettler et al. | |
| 6,110,483 A | 8/2000 | Whitbourne et al. | |
| 6,176,849 B1 | 1/2001 | Yang et al. | |
| 6,410,044 B1 | 6/2002 | Chudzik et al. | |
| 6,413,539 B1 | 7/2002 | Shalaby | |

(Continued)

*Primary Examiner*—Timothy H Meeks
*Assistant Examiner*—Cachet I Sellman
(74) *Attorney, Agent, or Firm*—Baker & Daniels LLP (57) ABSTRACT

A method for producing a zirconia-layered orthopedic implant component includes depositing zirconium onto the orthopedic implant component, thereby forming a zirconium-layered component, and converting at least a portion of the zirconium into a substantially monoclinic zirconia surface layer unaccompanied by a substantial underlying α-phase. A method for producing a zirconia-layered orthopedic implant component includes depositing zirconium onto the orthopedic implant component by ion bombardment and deposition in a vacuum to form a zirconium-layered component including an intermix zone at least 1000 Å thick and a zirconium layer about 3-5 μm thick, and heat treating the zirconium-layered component at a temperature of about 500-600° C. in an atmosphere containing oxygen.

23 Claims, 8 Drawing Sheets

U.S. PATENT DOCUMENTS 6,544,472 B1  4/2003  Compton
6,726,725 B2 *  4/2004  Hunter et al. ............ 623/23.54
6,974,625 B2 *  12/2005  Hunter et al. ............ 428/304.4
2003/0036794 A1  2/2003  Ragheb et al.

* cited by examiner

METHOD FOR PRODUCING A ZIRCONIA-LAYERED ORTHOPEDIC IMPLANT COMPONENT

FIELD OF THE INVENTION

The present invention relates generally to the field of orthopedics, and, more particularly, to a method for producing a zirconia-layered orthopedic implant component.

BACKGROUND

It is noted that basic chemical composition and/or formulae designations and the like are interchangeable with their respective generic compound, material, and/or element names throughout the following background, description, accompanying drawings, and the claims (for example: Zr is interchangeable with zirconium, O is interchangeable with oxygen, $ZrO_2$ is interchangeable with zirconia and/or zirconium oxide, Co—Cr—Mo is interchangeable with cobalt-chromium-molybdenum, Ti is interchangeable with titanium, $Y_2O_3$ is interchangeable with yttria, and MgO is interchangeable with magnesia).

The longevity of medical implant components is of prime importance as it is desirable that an implant should function for the complete lifetime of a patient. This is particularly pertinent if the patient is young and the number of surgical revisions is to be kept to a minimum and preferably zero. To this end, orthopedic implant materials should preferably combine high strength, corrosion resistance and tissue compatibility.

One of the variables affecting the longevity of load-bearing implants such as hip implants and knee implants is the rate of wear of the articulating surfaces and long-term effects of metal ion release. For example, a typical hip-joint prosthesis includes a stem, a femoral head and an acetabular cup against which the femoral head articulates. Wear of either the femoral head or the acetabular cup can result in an increasing level of wear particulates and "play" between the femoral head and the cup. Wear debris can contribute to adverse tissue reaction leading to bone resorption, such that ultimately the joint may need to be replaced. The rates of wear of the acetabular cup and the femoral head surfaces of artificial hips depend on a number of factors which include the relative hardness and surface finish of the materials constituting the femoral head and the acetabular cup, the frictional coefficient between the materials of the cup and head, the loads applied, and the stresses generated at the articulating surfaces.

The most common material combinations currently used in the fabrication of hip-joint implants include femoral heads of cobalt, titanium, or zirconium alloys articulating against acetabular cups lined with organic polymers or composites of such polymers including, for instance, ultra-high molecular weight polyethylene (UHMWPE) and femoral heads of polished alumina in combination with acetabular cups lined with an organic polymer or composite or made of polished alumina. Similarly, knee, shoulder, and elbow implants typically include metallic articulating components and polymeric bearings. Of the factors that influence rates of wear of conventional load-bearing implants, most significant are patient weight and activity level. Additionally, heat generated by friction in the normal operation of an implant has been shown to cause accelerated creep and wear of bearing components. In a typical hip-joint prosthesis, there is a correlation between the frictional moment that transfers torque loading to the acetabular cup and the frictional coefficient between the femoral head and the surface of the cup against which the head articulates. Cup torque has been associated with cup loosening. Thus, in general, the higher the coefficient of friction for a given load, the higher the level of torque generated. UHMWPE, being a polymeric material, is more susceptible to creep when heated than the metal alloys or ceramics commonly used to form opposing articulating surfaces due to its relatively lower melting point; consequently, it is more susceptible to wear than the alloys or ceramics.

Additionally, it has also been found that metal prostheses are not completely inert in the body. Body fluids act upon the metals causing them to slowly corrode by an ionization process thereby releasing metal ions into the body. Metal ion release from the prosthesis is also related to the articulation and rate of wear of load bearing surfaces because, as may be expected, when a metallic femoral head, for instance, is articulated against UHMWPE, the passive oxide film which forms on the femoral head is constantly removed. The repassivation process constantly releases metal ions during this process. Furthermore, the presence of third-body wear (cement or bone debris) may accelerate this process and micro fretted metal particles can increase friction. Consequently, the UHMWPE bearing components against which some conventional metallic surfaces articulate may be subjected to additionally accelerated levels of creep, wear, and torque.

There have been attempts to layer zirconia onto articulating surfaces of metallic orthopedic implant components to provide lower friction, higher wear resistance, and/or higher corrosion resistance. Zirconia (having a basic chemical composition of $ZrO_2$ and also sometimes called zirconium oxide) is a low-friction material that has performed positively in wear tests against polyethylene ("PE"). Another feature of $ZrO_2$ that should be noted is its isomeric phases. The phases are identical in terms of chemistry (all involve two O atoms to one Zr atom), but differ in crystal structure: monoclinic, tetragonal and cubic. At room temperature, the stable phase of $ZrO_2$ is the monoclinic. However, when heat is applied this transforms to tetragonal at about 950° C. Further heating of the tetragonal causes transformation to cubic at 2370° C. With additional heating the $ZrO_2$ melts at about 2600° C. Special processing of $ZrO_2$ can retain, at room temperature, the tetragonal or cubic phases. They are, however, thermodynamically metastable and can be transformed to monoclinic with suitable applied stress. When this happens, the $ZrO_2$ generally spalls and fractures because of a volume change. For example, when tetragonal $ZrO_2$ at room temperature is sufficiently stressed, its transformation to monoclinic involves a 4% volume change. Usually this causes the $ZrO_2$ to break apart. Other influences besides stress can (such as elevated temperatures and steam exposure during autoclaving, for example) can also cause transformation. If certain species are added to the pure $ZrO_2$, the tetragonal or even the cubic phase can be stabilized at temperatures and stress states in which they would otherwise be metastable (including room temperature). These species are called stabilizers and include yttria ($Y_2O_3$), magnesia (MgO) and calcium oxide (CaO). Addition of 2-4 wt % of any of these is sufficient to stabilize tetragonal $ZrO_2$ at room temperature. However, it is noted that the present invention does not employ such stabilizers. Thus, $ZrO_2$ has well established wear and friction advantages. Additionally, the inventors have observed no significant frictional or wear differences between the three phases. Nevertheless, successful uses of $ZrO_2$ depend largely upon its compatibility with other manufacturing processes and its stability against fracture and spalling.

Figure 1:
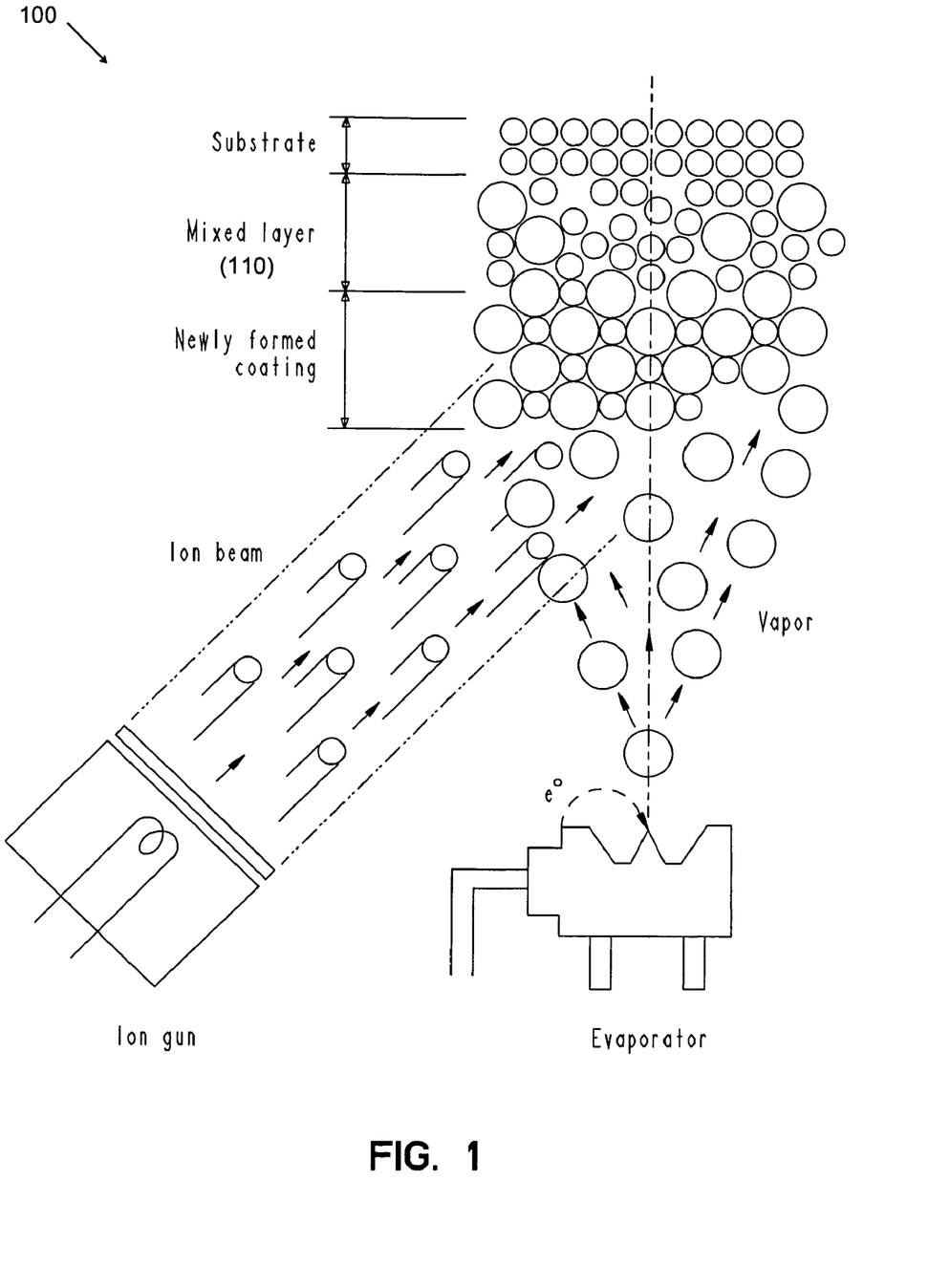
FIG. 1 shows a simplified illustration of an exemplary Ion Beam Assisted Deposition ("IBAD") setup.
Figure 2:
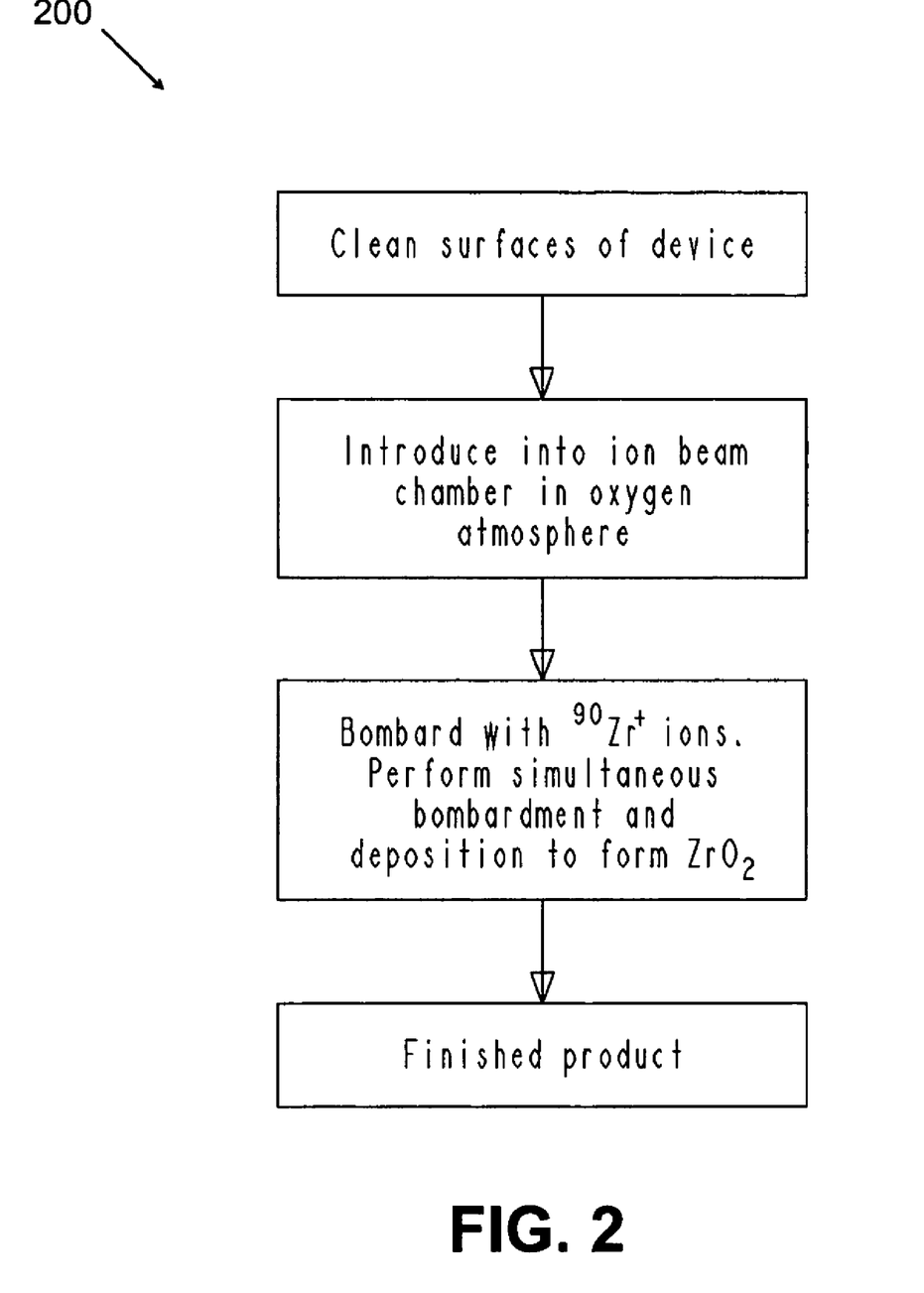
FIG. 2 shows a simplified block diagram of an exemplary IBAD process.

FIG. 1 shows a simplified illustration of an exemplary Ion Beam Assisted Deposition ("IBAD") setup 100 and FIG. 2 shows a simplified block diagram of an exemplary IBAD process 200. IBAD, which is one process that has been used to layer zirconia onto metallic orthopedic implant components, is a generic term for employing accelerated ions to drive a vapor phase into the surface of a substrate. Other IBAD applications beyond orthopedics have included superconductor processing work (at Los Alamos National Labs, among other places), and numerous surface treatments not only for wear resistance, but also corrosion resistance, and optical modification across a broad base of industry. IBAD is disclosed in U.S. Pat. No. 5,383,934 to Armini et al., issued Jan. 24, 1995 ("Armini"), among other patents. Armini is expressly incorporated herein by reference. Implant Sciences Corp. ("ISC") has been involved with IBAD technology as it relates to applying wear-resistance $ZrO_2$ to orthopaedic implants.

As at least partially discernable in FIG. 1 and FIG. 2, orthopedic devices receiving IBAD treatment are typically cleaned and then loaded into a vacuum chamber. The ion gun then first bombards the device surfaces with a beam of Zr+ ions with the vapor phase off. Some of the ions implant into the part surface to create an "intermix zone" 110 (see FIG. 1) of about 1000 Å deep. In the intermix zone 110, the Zr composition changes gradually from 0% to near 100%. The intermix zone 110 contributes to good adhesion of the eventual $ZrO_2$ layer. Next, with the ion beam still operating, neutral Zr atoms are introduced as a vapor. Simultaneously, $O_2$ gas (or $H_2O$ vapor) is introduced. The Zr and $O_2$ react at the substrate surface to form $ZrO_2$, and the ion beam drives most of these molecules into the surface. After about 8 hours, a 2 µm thick surface layer of $ZrO_2$ is formed. It is noted that this IBAD method differs from "regular" IBAD treatments in that a gas-phase reaction ($Zr+O_2 \rightarrow ZrO_2$) takes place. In fact, ISC prefers to call this process "ion beam reactive mixing" to distinguish it from other IBAD approaches. In any event, IBAD materials made in the ISC method have qualities and shortcomings.

Figure 3:
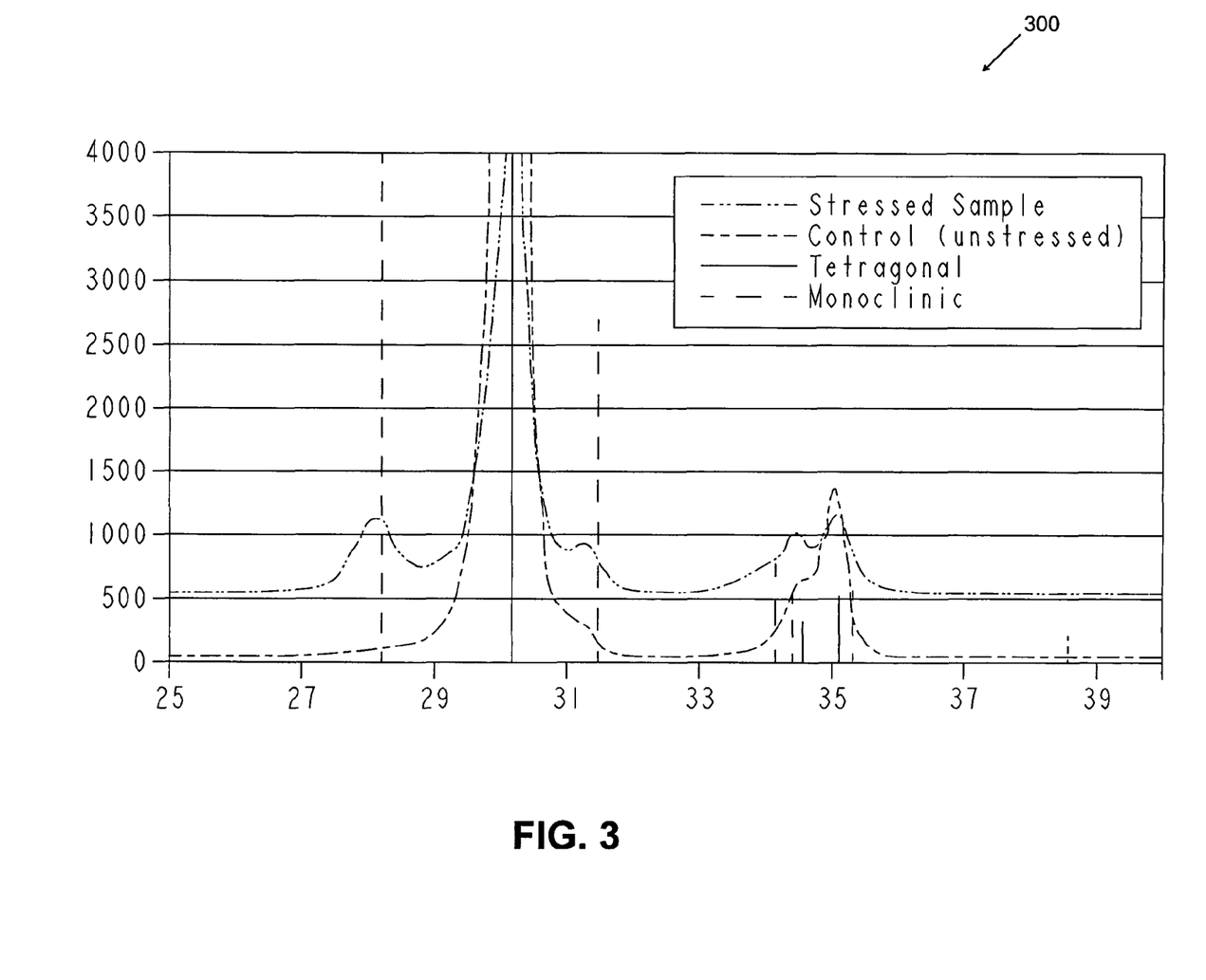
FIG. 3 shows a graph of exemplary X-ray diffraction patterns for transformation of tetragonal IBAD to monoclinic through application of 322 ksi peak compressive stress.

FIG. 3 shows a graph 300 of exemplary X-ray diffraction patterns for transformation of tetragonal IBAD to monoclinic through application of 322 ksi peak compressive stress. One of the most negative aspects of IBAD is that the final $ZrO_2$ is present as the metastable tetgragonal phase. This can be transformed to monoclinic via stress. Should such transformation occur in service, debris might be generated, and this might hasten wear of the PE through third-body effects.

On the other hand, the qualities of IBAD include the intermix zone (which resists delamination) and, unlike a process such as OXINIUM™, which is discussed below, IBAD is not restricted to only Zr-rich substrates. Finally, IBAD generally requires no post polishing, and may be more suitable for attachment of porous bone-in-growth materials.

Figure 4:
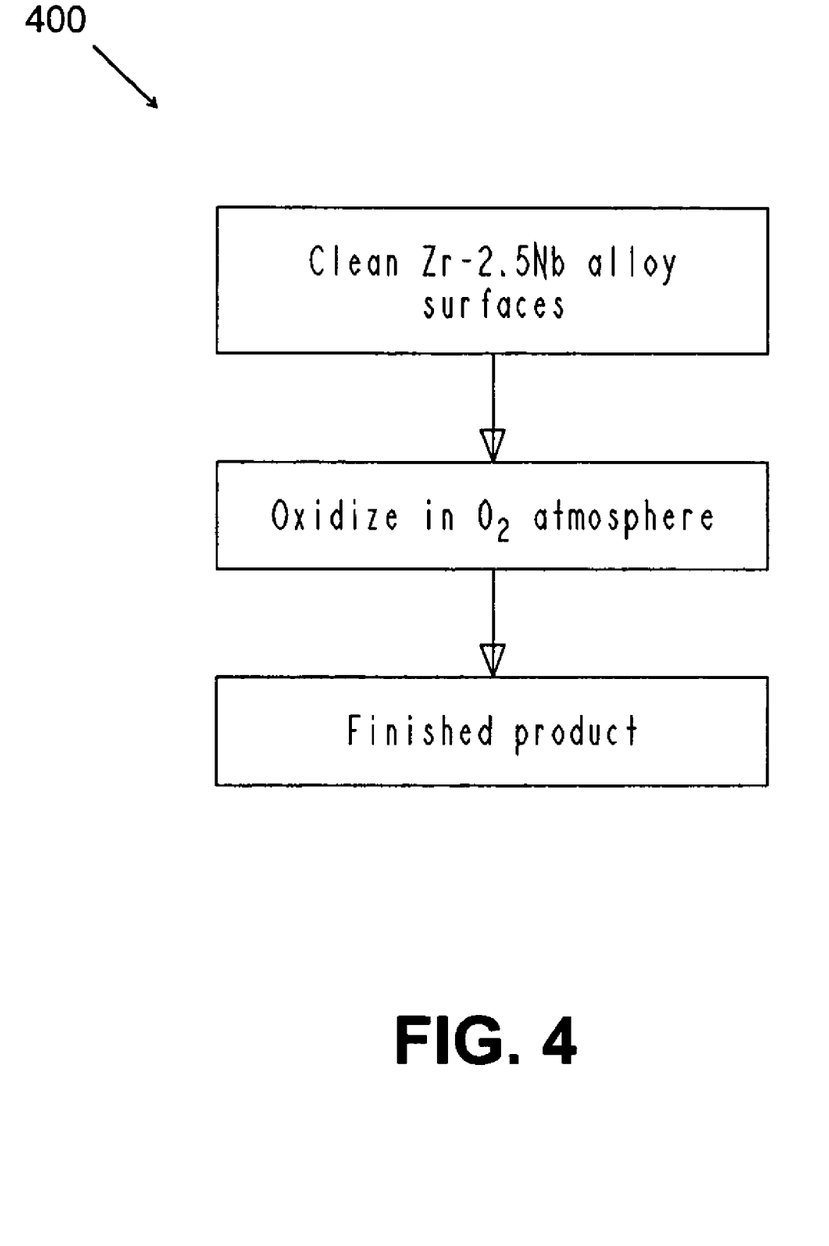
FIG. 4 shows a simplified block diagram of an exemplary OXINIUM™ process.

Next, FIG. 4 shows a simplified block diagram of an exemplary OXINIUM™ process 400 that has been used by Smith & Nephew. OXINIUM components consist of a Zr-2.5Nb alloy with a $ZrO_2$ surface layer of about 5 µm thickness. A typical OXINIUM component is first forged or machined from Zr-2.5Nb stock material. The component is then heated in air at about 1000° F. for about 3 hours. This is disclosed in U.S. Pat. No. 5,037,438 to Davidson, issued Aug. 6, 1991 ("Davidson"), which is expressly incorporated herein by reference. Alternatively, the component can be immersed in a molten salt bath that contains an oxidizer (typically $Na_2CO_3$) at 1290° F. for 4 hours. This is disclosed in U.S. Pat. No. 4,671,824 to Haygarth, issued Jun. 9, 1987 ("Haygarth"), which is expressly incorporated herein by reference. Whether air, salt or other, the oxidation of the Zr-2.5Nb alloy results in the $ZrO_2$ surface layer. In addition, Davidson discloses use of other alloys, including various Zircadyne and Zircalloy grades. Here, it is also noted that the general oxidation of Zr-rich alloys for improved wear performance was disclosed at least as early as U.S. Pat. No. 2,987,352 to Watson, issued Jun. 6, 1961 ("Watson"), which is expressly incorporated herein by reference. Watson involved a bearing application that took advantage of the low-friction characteristics of $ZrO_2$. Later, Zr and some Zr alloys became popular for use in corrosive and/or highly radioactive applications. One such alloy is Zr-2.5 Nb, known for its resistance to radiation damage. Surface oxidation of this and other Zr alloys for improved wear is disclosed in patents to Kemp (U.S. Pat. Nos. 5,316,594; 5,324,009; 5,399,207) and is a commercial offering called NOBLEIZING™. Valve parts for nuclear reactors are often made of Zr-2.5Nb (or similar) and subjected to a NOBLEIZING treatment.

OXINIUM also has both qualities and shortcomings as a bio-material. A noteworthy quality is that the $ZrO_2$ that forms during oxidation is in the stable monoclinic phase. OXINIUM is therefore resistant to stress/thermally-induced transformation in regular usage. This, in turn, removes risks of transformation-induced fracture and spalling due to normal orthopaedic stress and/or thermal situations. On the other hand, OXINIUM has notable shortcomings, including a $ZrO_2$ delamination potential, subsequent exposure of an inferior alloy (Zr-2.5Nb), a reported need to polish components after oxidation, and difficulty in attaching porous bone in-growth materials.

Thus, there is a general need for metallic orthopedic implant components with low friction, wear resistant, and corrosion resistant articulating surfaces and, more particularly, there is a need for a method for producing zirconia-layered orthopedic implant components that provides qualities similar to those of IBAD and OXINIUM without some of their shortcomings.

SUMMARY OF THE INVENTION

The present invention provides a method for producing a zirconia-layered orthopedic implant component including depositing zirconium onto the orthopedic implant component, thereby forming a zirconium-layered component, and converting at least a portion of the zirconium into a substantially monoclinic zirconia surface layer unaccompanied by a substantial underlying α-phase.

The present invention provides a method for producing a zirconia-layered orthopedic implant component including depositing zirconium onto the orthopedic implant component by ion bombardment and deposition in a vacuum to form a zirconium-layered component including an intermix zone at least 1000 Å thick and a zirconium layer about 3-5 µm thick, and heat treating the zirconium-layered component at a temperature of about 500-600° C. in an atmosphere containing oxygen.

The above-noted features and advantages of the present invention, as well as additional features and advantages, will be readily apparent to those skilled in the art upon reference to the following detailed description and the accompanying drawings, which include a disclosure of the best mode of making and using the invention presently contemplated.

BRIEF DESCRIPTION OF THE DRAWINGS

FIG. 6 shows an exemplary Zr—O equilibrium phase diagram;

DETAILED DESCRIPTION OF EXEMPLARY EMBODIMENT(S)

Like reference numerals refer to like parts throughout the following description, the accompanying drawings, and the claims. Additionally, as noted above, basic chemical composition and/or formulae designations and the like are interchangeable with their respective generic compound, material, and/or element names throughout the foregoing background and the following description, accompanying drawings, and the claims (for example: Zr is interchangeable with zirconium, O is interchangeable with oxygen, $ZrO_2$ is interchangeable with zirconia and/or zirconium oxide, Co—Cr—Mo is interchangeable with cobalt-chromium-molybdenum, Ti is interchangeable with titanium, $Y_2O_3$ is interchangeable with yttria, and MgO is interchangeable with magnesia).

As discussed further below, in the exemplary embodiment the present invention provides a metallic orthopedic implant component (for example, a femoral knee component or femoral hip heads, or other metallic orthopedic component) with a $ZrO_2$ surface treatment. The inventors prefer $ZrO_2$ because of its relative ease of production, biocompatibility, and its clinical evidence as a low-friction bearing material. However, it is also noted that the principles of the present invention may be expanded to include the application of practically any suitable surface material, beyond $ZrO_2$, that improves wear of an orthopaedic device. Such candidates include alumina (having a basic chemical composition of $Al_2O_3$), titanium oxide (for example, having a basic chemical composition of $TiO_2$), and titanium nitride (having a basic chemical composition of TiN), among others. Further, it is noted that the implant components ("substrates" or "devices") may be made from cobalt-chromium-molybdenum alloys (having a basic chemical composition of Co—Cr—Mo and also referred to herein as "CCM"), Ti, Ti alloys, stainless steels, and/or any other suitable material(s).

Figure 5:
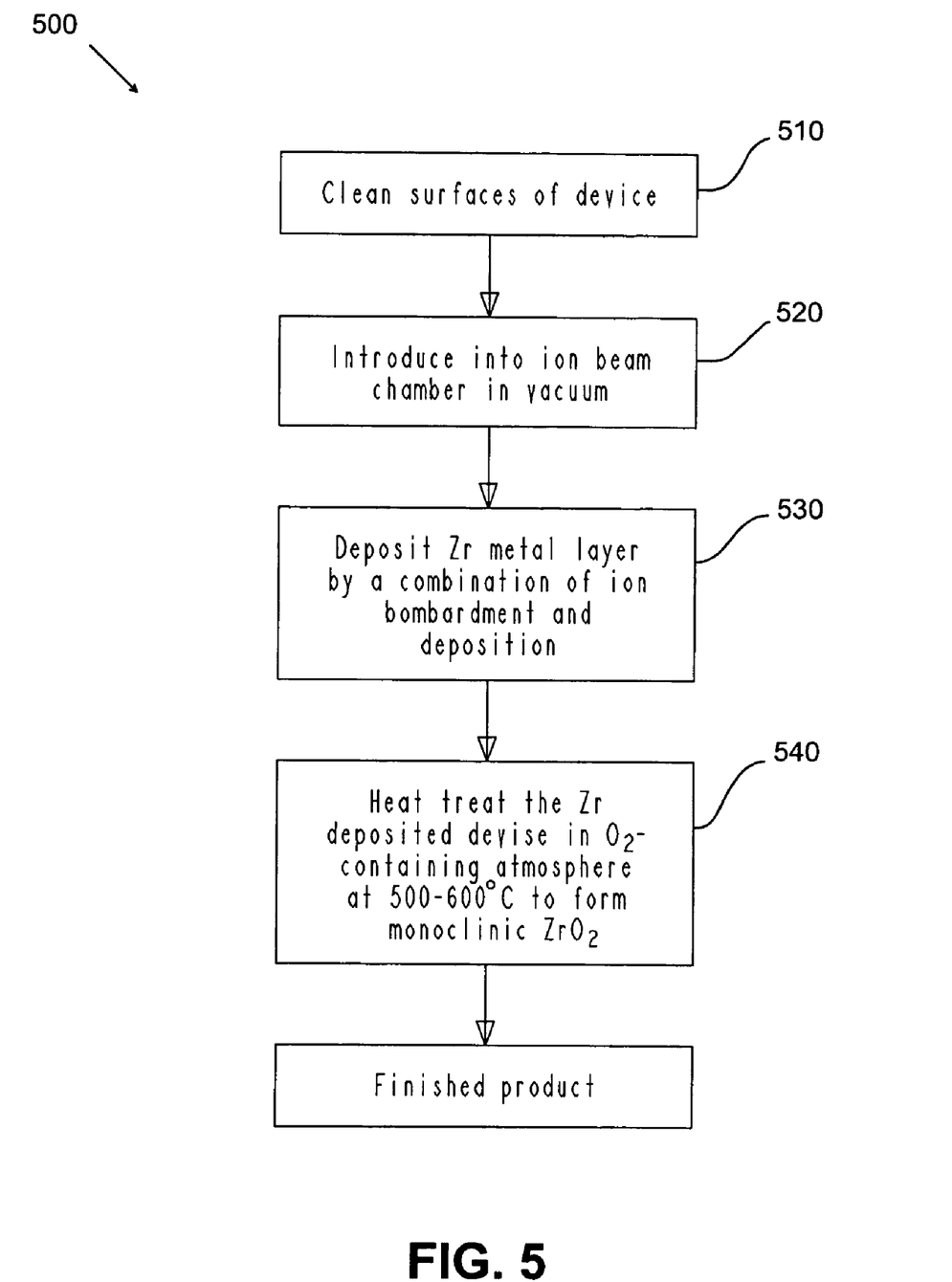
FIG. 5 shows a simplified block diagram of an exemplary method 500 according to the present invention.

FIG. 5 shows a simplified block diagram of an exemplary method 500 according to the present invention. In step 510, the metallic orthopedic component ("device") being processed is cleaned in a known manner to remove as much dirt and/or oxidation as is practical. Via steps 520 and step 530, zirconium is deposited onto the device, thereby forming a zirconium-layered component. In the preferred embodiment, steps 520 and 530 are performed according to the above-discussed IBAD process, wherein the device is introduced into an evacuated ion bean chamber (step 520) and a Zr layer is deposited onto the device in the vacuum by a combination of ion bombardment and deposition to form a zirconium-layered component including an intermix zone at least 1000 Å thick and a zirconium layer about 3-5 μm thick (step 530). The preference for the IBAD lies in its relatively easy achievement of the 1000 Å minimum intermix zone. Additionally, it should be appreciated that the vacuum inhibits re-oxidation of the device before the Zr layer is established. However, alternative embodiments may include any other suitable means to inhibit re-oxidation and/or deposit Zr onto the device. Beyond the IBAD of the preferred embodiment, such alternative methods may include other physical deposition methods (which may include another IBAD method), chemical vapor deposition, plasma-enhanced magnetron sputter deposition, diffusion cladding, electron beam deposition, electrochemical, among others.

Next, in step 540, at least a portion of the zirconium is converted into a substantially monoclinic zirconia surface layer unaccompanied by a substantial underlying "α-phase." The avoided α-phase is discussed further below. Preferably, step 540 is accomplished by post-oxidizing the zirconium-layered component to form a $ZrO_2$ surface layer using a method similar to that for OXINIUM (discussed above), wherein the zirconium-layered component is heat treated the at a temperature of about 500-600° C. in an atmosphere containing a suitable amount of oxygen for about 3-4 hours or any other suitable time period.

Thus, as should be further appreciated from the following discussion, components produced according to the exemplary embodiment of FIG. 5 have the good $ZrO_2$ adhesion characteristics of IBAD (due primarily to the intermix zone) with the stable, fracture- and spall-resistant monoclinic $ZrO_2$ phase characteristics of OXINIUM. First, formation of the Zr intermix layer (steps 520 and 530) is consistent with regular IBAD processing. Equipment capable of supplying an adequate intermixed 3-5 μm thick Zr layer onto a metallic substrate is widely available and manners for doing so are known.

Figure 6:
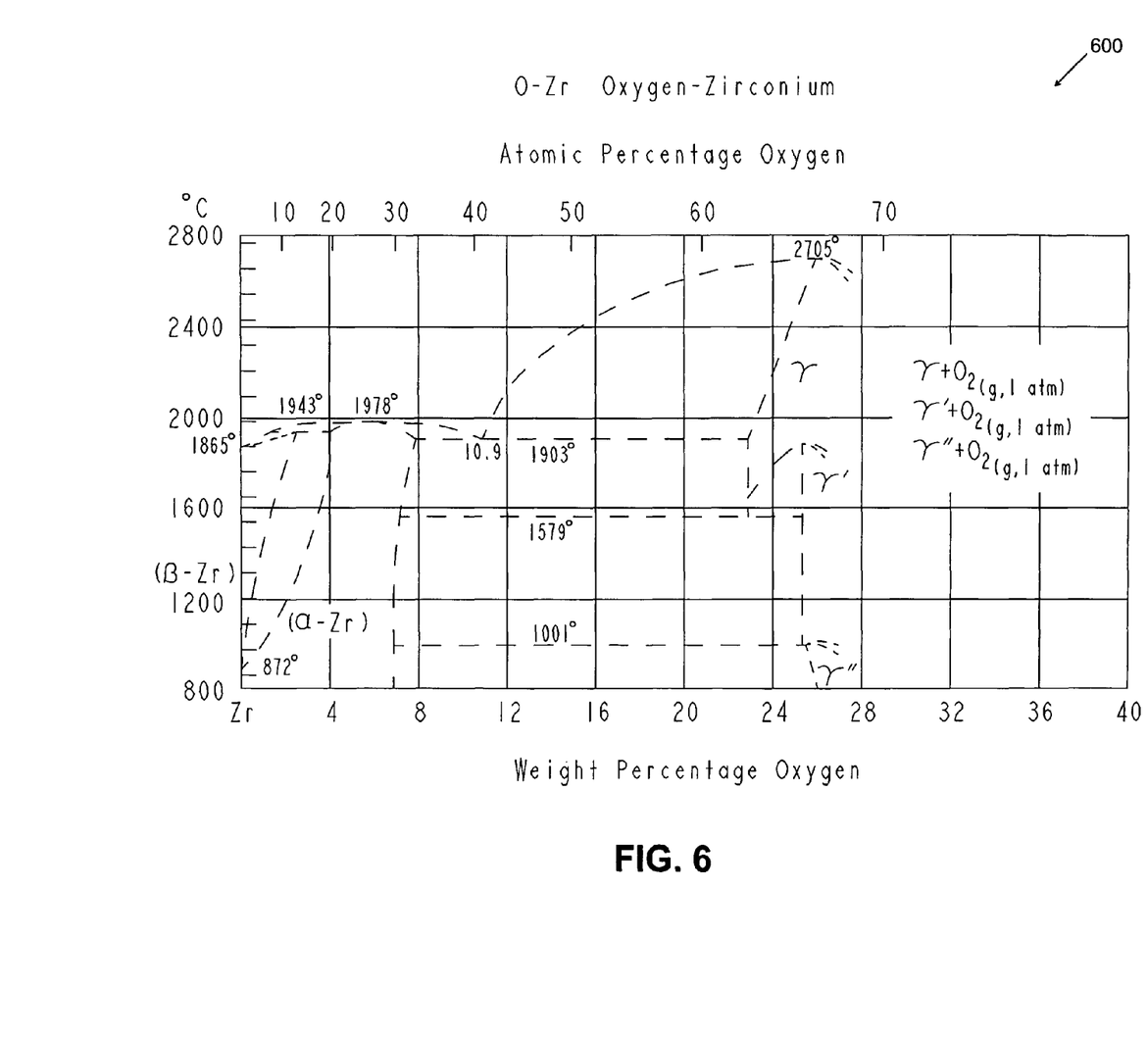

Next, FIG. 6 shows an exemplary Zr—O equilibrium phase diagram 600. Although the post-oxidation of the exemplary embodiment (FIG. 5, step 540) has much in common with OXINIUM, it also has notable differences. The sequence of events during OXINIUM processing is predictable from diagram 600. The first oxide phase to form at the reported OXINIUM process temperature (1000° F., 537° C.) is the α-phase. This is not $ZrO_2$ but rather a solid solution of O atoms dissolved in the Zr lattice. The phase diagram shows that O can dissolve in Zr up to a limit around 7 wt % 0. Once the O content exceeds 7%, monoclinic $ZrO_2$ abruptly forms. The phase diagram shows that $ZrO_2$ contains about 27 wt % O. The monoclinic $ZrO_2$ phase appears as γ" in this diagram. Moreover, the phase diagram predicts that a surface layer of monoclinic $ZrO_2$ is always accompanied by an underlying layer of α-phase. Between the two is an interface across which the O content changes abruptly from 27 wt % to 7 wt %. This sharp O transition would likely result in a sharp change in mechanical properties. As such, when OXINIUM is subjected to large applied loads, the interface has the potential to fracture and cause spalling of the $ZrO_2$ surface layer.

Figure 7:
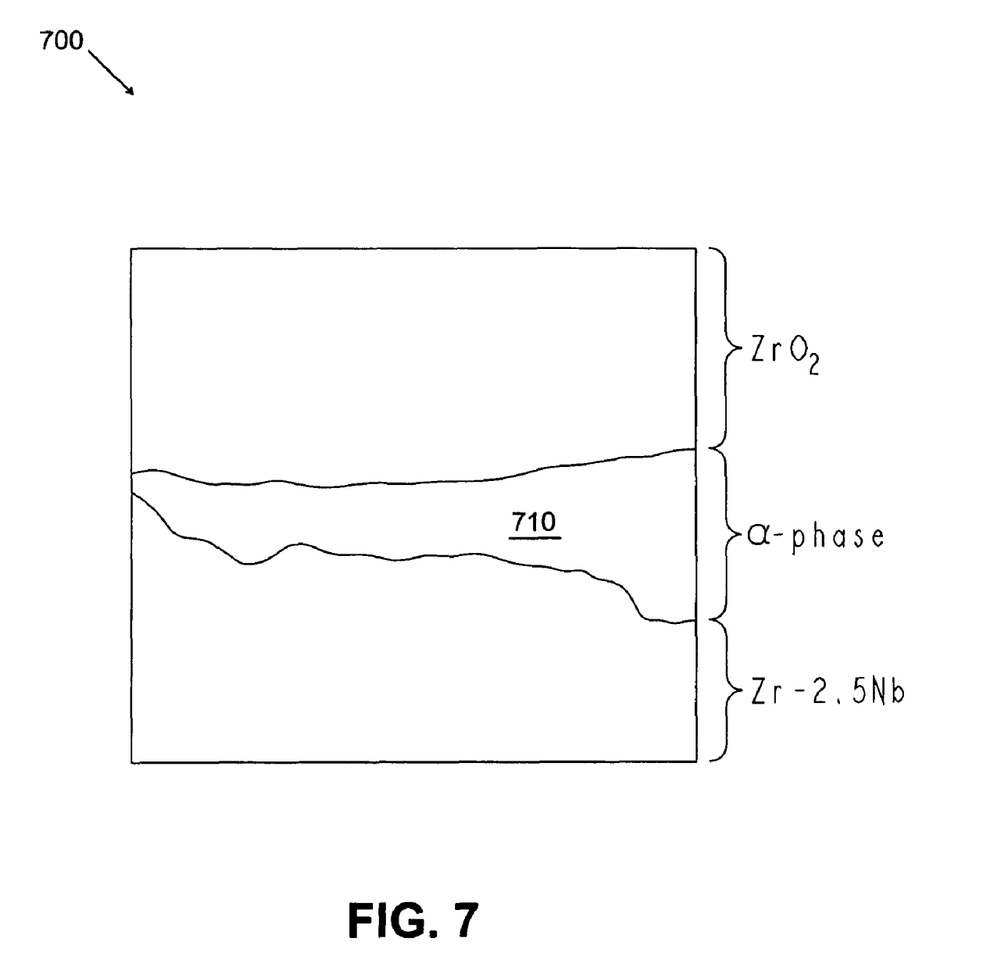
FIG. 7 shows an illustration of an exemplary simplified OXINIUM cross-section including an exemplary α-phase.

FIG. 7 shows an illustration of an exemplary simplified OXINIUM cross-section 700 including an exemplary α-phase 710. Relative to OXINIUM, IBAD appears to be far less susceptible to delamination by virtue of its intermix zone 110 and lack of an α-phase (see FIG. 1). Accordingly, the present invention shares the layer characteristics of IBAD even though surface oxidation will be similar to OXINIUM. One reason is because the present invention provides an intermix zone, helping promote a gradual O transition from 27% to 0%. Another reason is because the present invention includes a modified post-oxidation process. Zr has a high affinity to react with oxygen. Zr is often used as a "getter" material in heat treating operations to remove residual oxygen from the heat treat atmosphere. In this way the (non-Zr) workpiece is protected from oxidation. The present invention exploits this getter phenomenon as a way to convert the entire surface Zr to $ZrO_2$ without forming an α-phase in the final product, and without oxidizing the substrate.

Figure 8:
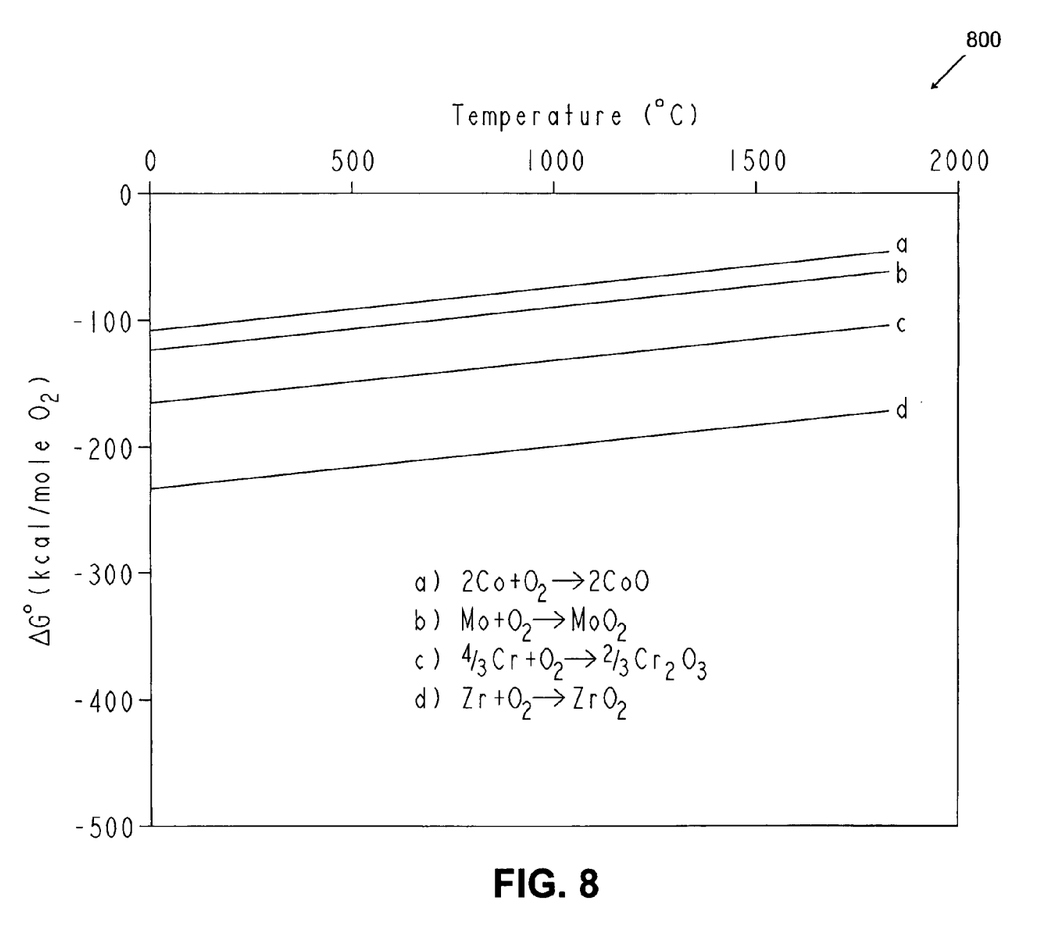
FIG. 8 shows an exemplary Ellingham diagram for the free energy of metal oxidation.

FIG. 8 shows an exemplary Ellingham diagram 800 for the free energy of metal oxidation. The getter phenomenon of Zr relative to Co, Cr and Mo is at least partially discernable from diagram 800. At a given temperature, this diagram displays the free energy change ($\Delta G°$) of oxidation for Zr, Cr, Co, and Mo oxides. The lower (more negative) the $\Delta G°$, the higher the affinity for oxygen. As the diagram shows, Zr has much higher affinity for oxygen than Co, Cr, or Mo. Therefore, the proper combination of temperature and oxidizing condition oxidizes all of the Zr to $ZrO_2$ (including the intermix zone) without oxidizing a CCM substrate.

Additionally, it is noted that some components processed according to the exemplary embodiment of the present invention, notably femoral knees, may also require a bone in-growth surface for cementless applications. From a manufacturing standpoint, the attachment of the porous in-growth medium should be compatible with the $ZrO_2$ formation. OXINIUM components, being made wholly from a Zr-rich alloy, form $ZrO_2$ on all surfaces (articular and box-cut). The presence of the $ZrO_2$ ceramic on the box-cut surface has apparently precluded the ability to attach regular bone in-growth media (such as porous plasma spray) because of poor adhesion. The present invention should provide an advantage in this regard. With the present invention, $ZrO_2$ forms only where Zr was introduced, namely, for example, the articulating surface. A box-cut surface that remains free from Zr is susceptible only to possible Cr, Co or Mo oxidation, which may be avoided through proper selection of oxidation conditions (see FIG. 8). Further, it is noted that masking of the box-cut surface with a heat-resistant paint (e.g., "Stop-Off") may help prevent box-cut oxidation.

EXPRESSLY INCORPORATED REFERENCES: All patents and/or publications mentioned in the specification are indicative of the level of those skilled in the art to which the invention pertains. All such mentioned patents and/or publications, including but not limited to the following references, are herein incorporated by reference to the same extent as if each individual references was specifically and individually indicated to be incorporated by reference:

U.S. Pat. No. 6,726,725 to Hunter et al., issued Apr. 27, 2004;
U.S. Pat. No. 5,383,934 to Armini et al., issued Jan. 24, 1995;
U.S. Pat. No. 5,037,438 to Davidson, issued Aug. 6, 1991;
U.S. Pat. No. 4,671,824 to Haygarth, issued Jun. 9, 1987;
U.S. Pat. No. 4,145,764 to Suzuki et al., issued Mar. 27, 1979;
U.S. Pat. No. 3,677,795 to Bokros et al., issued Jul. 18, 1972; and
U.S. Pat. No. 2,987,352 to Watson, issued Jun. 6, 1961.

The foregoing description of the invention is illustrative only, and is not intended to limit the scope of the invention to the precise terms set forth. Further, although the invention has been described in detail with reference to certain illustrative embodiments, variations and modifications exist within the scope and spirit of the invention as described and defined in the following claims.

What is claimed is:

1. A method for producing a zirconia-layered orthopedic implant component, the method comprising the steps of:
   depositing zirconium onto the orthopedic implant component, thereby forming a zirconium-layered component having an intermix zone and a zirconium layer; and
   converting at least a portion of the zirconium into a substantially monoclinic zirconia surface layer unaccompanied by a substantial underlying α-phase by heat treating the zirconium-layered component in an atmosphere containing oxygen at atmospheric pressure.

2. The method of claim 1, wherein the depositing step includes inhibiting oxidation of the orthopedic implant component.

3. The method of claim 2, wherein the depositing step includes depositing the zirconium onto the orthopedic implant component in a vacuum.

4. The method of claim 1, wherein the intermix zone is at least 1000 Å thick and the zirconium layer is about 3-5 μm thick.

5. The method of claim 1, wherein the converting step includes heat treating the zirconium-layered component at a temperature of about 500-600° C.

6. The method of claim 5, wherein the converting step includes heat treating the zirconium-layered component for about 3-4 hours.

7. A method for producing a zirconia-layered orthopedic implant component, the method comprising the steps of:
   depositing zirconium onto the orthopedic implant component, thereby forming a zirconium-layered component, wherein the depositing step includes depositing the zirconium onto the orthopedic implant component by ion bombardment and deposition; and
   converting at least a portion of the zirconium into a substantially monoclinic zirconia surface layer unaccompanied by a substantial underlying α-phase by heat treating the zirconium-layered component in an atmosphere containing oxygen at atmospheric pressure.

8. The method of claim 7, wherein the depositing step includes depositing the zirconium onto the orthopedic implant component such that zirconium-layered component includes an intermix zone being at least 1000 Å thick and further includes a zirconium layer being about 3-5 μm thick.

9. The method of claim 8, wherein the converting step includes heat treating the zirconium-layered component at a temperature of about 500-600° C.

10. The method of claim 9, wherein the converting step includes heat treating the zirconium-layered component for about 3-4 hours.

11. The method of claim 10, wherein the depositing step includes depositing the zirconium onto the orthopedic implant component in a vacuum.

12. The method of claim 11, wherein the depositing step includes depositing the zirconium onto a cobalt-chromium-molybdenum alloy.

13. The method of claim 12, wherein the depositing step includes depositing the zirconium onto at least one of a hip implant component, a knee implant component, a shoulder implant component, and an elbow implant component.

14. The method of claim 11, wherein the depositing step includes depositing the zirconium onto at least one of a titanium alloy and a stainless steel.

15. The method of claim 14, wherein the depositing step includes depositing the zirconium onto at least one of a hip implant component, a knee implant component, a shoulder implant component, and an elbow implant component.

16. A method for producing a zirconia-layered orthopedic implant component, the method comprising the steps of:
   depositing zirconium onto the orthopedic implant component by ion bombardment and deposition to form a zirconium-layered component including an intermix zone at least 1000 Å thick and a zirconium layer about 3-5 μm thick; and heat treating the zirconium-layered component at a temperature of about 500-600° C. in an atmosphere containing oxygen at atmospheric pressure.

17. The method of claim 16, wherein the heat treating step includes heat treating the zirconium-layered component for about 3-4 hours.

18. The method of claim 17, further comprising the step of cleaning the orthopedic implant component before the depositing step.

19. The method of claim 18, wherein the depositing step includes depositing the zirconium onto a cobalt-chromium-molybdenum alloy.

20. The method of claim 19, wherein the depositing step includes depositing the zirconium onto at least one of a hip implant component, a knee implant component, a shoulder implant component, and an elbow implant component.

21. The method of claim 18, wherein the depositing step includes depositing the zirconium onto at least one of a titanium alloy and a stainless steel.

22. The method of claim 21, wherein the depositing step includes depositing the zirconium onto at least one of a hip implant component, a knee implant component, a shoulder implant component, and an elbow implant component.

23. The method of claim 16, wherein the depositing further comprises depositing zirconium onto the orthopedic implant component by ion bombardment and deposition in a vacuum.

* * * * *